US008741610B2

(12) United States Patent
Onishi et al.

(10) Patent No.: US 8,741,610 B2
(45) Date of Patent: Jun. 3, 2014

(54) YEAST MUTANT AND SUBSTANCE PRODUCTION METHOD USING THE SAME

(75) Inventors: Toru Onishi, Toyota (JP); Nobuki Tada, Miyoshi (JP); Hibiki Matsushita, Nagoya (JP); Noriko Yasutani, Nagoya (JP); Nobuhiro Ishida, Seto (JP); Takashi Shimamura, Toyota (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 379 days.

(21) Appl. No.: 12/989,359

(22) PCT Filed: Apr. 23, 2009

(86) PCT No.: PCT/JP2009/058078
§ 371 (c)(1),
(2), (4) Date: Oct. 22, 2010

(87) PCT Pub. No.: WO2009/131179
PCT Pub. Date: Oct. 29, 2009

(65) Prior Publication Data
US 2011/0039316 A1 Feb. 17, 2011

(30) Foreign Application Priority Data

Apr. 23, 2008 (JP) ................................. 2008-113053

(51) Int. Cl.
*C12P 7/56* (2006.01)
(52) U.S. Cl.
USPC ................ 435/139; 435/7.1; 435/6; 435/252; 435/320.1
(58) Field of Classification Search
None
See application file for complete search history.

(56) References Cited

U.S. PATENT DOCUMENTS

| 6,040,160 | A | 3/2000 | Kojima et al. | |
|---|---|---|---|---|
| 6,190,914 | B1 * | 2/2001 | Grivell et al. | 435/483 |
| 6,429,006 | B1 * | 8/2002 | Porro et al. | 435/254.2 |
| 6,485,947 | B1 | 11/2002 | Rajgarhia et al. | |
| 7,534,597 | B2 | 5/2009 | Hause et al. | |
| 8,039,238 | B2 * | 10/2011 | Saito et al. | 435/136 |

FOREIGN PATENT DOCUMENTS

| JP | 2001-505777 A | 5/2001 |
|---|---|---|
| JP | 2001-516584 A | 10/2001 |
| JP | 2002-136293 A | 5/2002 |
| JP | 2003-500062 A | 1/2003 |
| JP | 2004-113004 A | 4/2004 |
| JP | 2005-528106 A | 9/2005 |
| JP | 2006-006271 A | 1/2006 |
| JP | 2008-043325 A | 2/2008 |
| JP | 2008-048726 A | 3/2008 |
| WO | 95/16042 A1 | 6/1995 |
| WO | 98/21340 A1 | 5/1998 |
| WO | 98/26079 A1 | 6/1998 |
| WO | 99/14335 A1 | 3/1999 |
| WO | 01-503634 A | 3/2001 |
| WO | 03/102152 A2 | 12/2003 |

OTHER PUBLICATIONS

Bourgarel et al. (Mol. Microbiol., 1999, vol. 31(4), pp. 1205-1215.*
Ishida et al. (Applied & Environ. Microbiol., 2005, 71(4), pp. 1964-1970).*
Brons et al. (Yeast, 2002, vol. 19, pp. 923-932).*
Nobuhiro Ishida, et al., "The Effect of Pyruvate Decarboxylase Gene Knockout in *Saccharomyces cerevisiae* on $_L$-Lactic Acid Production", Biosci. Biotechnol. Biochem., 2006, pp. 1148-1153, vol. 70, No. 5.
Antonius J. A. van Maris, et al., "Homofermentative Lactate Production Cannot Sustain Anaerobic Growth of Engineered *Saccharomyces cerevisiae*: Possible Consequence of Energy-Dependent Lactate Export", Applied and Environmental Microbiology, May 2004, pp. 2898-2905, vol. 70, No. 5.
International Search Report PCT/JP2009/058078, Jun. 9, 2009.
A Van Maris: "Modulating the distribution of fluxes among respiration and fermentation by overexpression of HAP4 in *Saccharomyces cerevisiae*", FEMS Yeast Research, vol. 1, No. 2, Jul. 1, 2001, pp. 139-149; XP55012720, ISSN: 1567-1356, DOI: 10.1016/S1567-1356(01)00022-8.
Extended European Search Report for corresponding EP Patent Application No. 09733795.0 dated Nov. 30, 2011.

* cited by examiner

*Primary Examiner* — Hope Robinson
(74) *Attorney, Agent, or Firm* — Sughrue Mion, PLLC

(57) ABSTRACT

The present invention provides, inter alia, an improvement in the production of a desired product from yeast, wherein the growth rate and fermentation rate of the yeast are maintained at excellent levels. The present invention also provides, inter alia, for the introduction of a foreign gene into a yeast host cell, wherein the foreign gene encodes an enzyme involved in the production of a desired product. The yeast may also constitutively express a HAP4 gene, or a homologous gene thereof, to significantly improve the ability of the yeast to produce the desired product while maintaining its growth rate and fermentation rate. In some embodiments, a yeast mutant is used which is a mutant strain having lowered alcohol productivity vis-à-vis a wild-type strain.

6 Claims, 5 Drawing Sheets

SEQUENCE LISTING

```
<160> NUMBER OF SEQ ID NOS: 37

<210> SEQ ID NO 1
<211> LENGTH: 1665
<212> TYPE: DNA
<213> ORGANISM: Saccharomyces cerevisiae
<220> FEATURE:
<221> NAME/KEY: CDS
<222> LOCATION: (1)..(1665)

<400> SEQUENCE: 1 atg acc gca aag act ttt cta cta cag gcc tcc gct agt cgc cct cgt      48
Met Thr Ala Lys Thr Phe Leu Leu Gln Ala Ser Ala Ser Arg Pro Arg
1               5                   10                  15 agt aac cat ttt aaa aat gag cat aat aat att cca ttg gcg cct gta      96
Ser Asn His Phe Lys Asn Glu His Asn Asn Ile Pro Leu Ala Pro Val
            20                  25                  30 ccg atc gcc cca aat acc aac cat cat aac aat agt tcg ctg gaa ttc     144
Pro Ile Ala Pro Asn Thr Asn His His Asn Asn Ser Ser Leu Glu Phe
        35                  40                  45 gaa aac gat ggc agt aaa aag aag aag tct agc ttg gtg gtt aga          192
Glu Asn Asp Gly Ser Lys Lys Lys Lys Ser Ser Leu Val Val Arg
    50                  55                  60 act tca aaa cat tgg gtt ttg ccc cca aga cca aga cct ggt aga aga     240
Thr Ser Lys His Trp Val Leu Pro Pro Arg Pro Arg Pro Gly Arg Arg
65                  70                  75                  80 tca tct tct cac aac act cta cct gcc aac aac acc aat aat att tta     288
Ser Ser Ser His Asn Thr Leu Pro Ala Asn Asn Thr Asn Asn Ile Leu
                85                  90                  95 aat gtt ggc cct aac agc agg aac agt agt aat aat aat aat aat aat     336
Asn Val Gly Pro Asn Ser Arg Asn Ser Ser Asn Asn Asn Asn Asn Asn
            100                 105                 110 aac atc att tcg aat agg aaa caa gct tcc aaa gaa aag agg aaa ata     384
Asn Ile Ile Ser Asn Arg Lys Gln Ala Ser Lys Glu Lys Arg Lys Ile
```

```
                     115                 120                 125
cca aga cat atc cag aca atc gat gaa aag cta ata aac gac tcg aat    432
Pro Arg His Ile Gln Thr Ile Asp Glu Lys Leu Ile Asn Asp Ser Asn
        130                 135                 140 tac ctc gca ttt ttg aag ttc gat gac ttg gaa aat gaa aag ttt cat    480
Tyr Leu Ala Phe Leu Lys Phe Asp Asp Leu Glu Asn Glu Lys Phe His
145                 150                 155                 160 tct tct gcc tcc tcc att tca tct cca tct tat tca tct cca tct ttt    528
Ser Ser Ala Ser Ser Ile Ser Ser Pro Ser Tyr Ser Ser Pro Ser Phe
                165                 170                 175 tca agt tat aga aat aga aaa aaa tca gaa ttc atg gac gat gaa agc    576
Ser Ser Tyr Arg Asn Arg Lys Lys Ser Glu Phe Met Asp Asp Glu Ser
        180                 185                 190 tgc acc gat gtg gaa acc att gct gct cac aac agt ctg cta aca aaa    624
Cys Thr Asp Val Glu Thr Ile Ala Ala His Asn Ser Leu Leu Thr Lys
            195                 200                 205 aac cat cat ata gat tct tct tca aat gtt cac gca cca ccc acg aaa    672
Asn His His Ile Asp Ser Ser Ser Asn Val His Ala Pro Pro Thr Lys
        210                 215                 220 aaa tca aag ttg aac gac ttt gat tta ttg tcc tta tct tcc aca tct    720
Lys Ser Lys Leu Asn Asp Phe Asp Leu Leu Ser Leu Ser Ser Thr Ser
225                 230                 235                 240 tca tcg gcc act ccg gtc cca cag ttg aca aaa gat ttg aac atg aac    768
Ser Ser Ala Thr Pro Val Pro Gln Leu Thr Lys Asp Leu Asn Met Asn
                245                 250                 255 cta aat ttt cat aag atc cct cat aag gct tca ttc cct gat tct cca    816
Leu Asn Phe His Lys Ile Pro His Lys Ala Ser Phe Pro Asp Ser Pro
            260                 265                 270 gca gat ttc tct cca gca gat tca gtc tcg ttg att aga aac cac tcc    864
Ala Asp Phe Ser Pro Ala Asp Ser Val Ser Leu Ile Arg Asn His Ser
        275                 280                 285 ttg cct act aat ttg caa gtt aag gac aaa att gag gat ttg aac gag    912
Leu Pro Thr Asn Leu Gln Val Lys Asp Lys Ile Glu Asp Leu Asn Glu
290                 295                 300 att aaa ttc ttt aac gat ttc gag aaa ctt gag ttt ttc aat aag tat    960
Ile Lys Phe Phe Asn Asp Phe Glu Lys Leu Glu Phe Phe Asn Lys Tyr
305                 310                 315                 320 gcc aaa gtc aac acg aat aac gac gtt aac gaa aat aat gat ctc tgg   1008
Ala Lys Val Asn Thr Asn Asn Asp Val Asn Glu Asn Asn Asp Leu Trp
                325                 330                 335 aat tct tac tta cag tct atg gac gat aca aca ggt aag aac agt ggc   1056
Asn Ser Tyr Leu Gln Ser Met Asp Asp Thr Thr Gly Lys Asn Ser Gly
            340                 345                 350 aat tac caa caa gtg gac aat gac gat aat atg tct tta ttg aat ctg   1104
Asn Tyr Gln Gln Val Asp Asn Asp Asp Asn Met Ser Leu Leu Asn Leu
        355                 360                 365 cca att ttg gag gaa acc gta tct tca ggg caa gat gat aag gtt gag   1152
Pro Ile Leu Glu Glu Thr Val Ser Ser Gly Gln Asp Asp Lys Val Glu
370                 375                 380 cca gat gaa gaa gac att tgg aat tat tta cca agt tca agt tca caa   1200
Pro Asp Glu Glu Asp Ile Trp Asn Tyr Leu Pro Ser Ser Ser Ser Gln
385                 390                 395                 400 caa gaa gat tca tca cgt gct ttg aaa aaa aat act aat tct gag aag   1248
Gln Glu Asp Ser Ser Arg Ala Leu Lys Lys Asn Thr Asn Ser Glu Lys
                405                 410                 415 gcg aac atc caa gca aag aac gat gaa acc tat ctg ttt ctt cag gat   1296
Ala Asn Ile Gln Ala Lys Asn Asp Glu Thr Tyr Leu Phe Leu Gln Asp
            420                 425                 430 cag gat gaa agc gct gat tcg cat cac cat gac gag tta ggt tca gaa   1344
Gln Asp Glu Ser Ala Asp Ser His His His Asp Glu Leu Gly Ser Glu
```

```
              435                 440                 445
atc act ttg gct gac aat aag ttt tct tat ttg ccc cca act cta gaa    1392
Ile Thr Leu Ala Asp Asn Lys Phe Ser Tyr Leu Pro Pro Thr Leu Glu
    450                 455                 460 gag ttg atg gaa gag cag gac tgt aac aat ggc aga tct ttt aaa aat    1440
Glu Leu Met Glu Glu Gln Asp Cys Asn Asn Gly Arg Ser Phe Lys Asn
465                 470                 475                 480 ttc atg ttt tcc aac gat acc ggt att gac ggt agt gcc ggt act gat    1488
Phe Met Phe Ser Asn Asp Thr Gly Ile Asp Gly Ser Ala Gly Thr Asp
                485                 490                 495 gac gac tac acc aaa gtt ctg aaa tcc aaa aaa att tct acg tcg aag    1536
Asp Asp Tyr Thr Lys Val Leu Lys Ser Lys Lys Ile Ser Thr Ser Lys
            500                 505                 510 tcg aac gct aac ctt tat gac tta aac gat aac aac aat gat gca act    1584
Ser Asn Ala Asn Leu Tyr Asp Leu Asn Asp Asn Asn Asn Asp Ala Thr
        515                 520                 525 gcc acc aat gaa ctt gat caa agc agt ttc atc gac gac ctt gac gaa    1632
Ala Thr Asn Glu Leu Asp Gln Ser Ser Phe Ile Asp Asp Leu Asp Glu
    530                 535                 540 gat gtc gat ttt tta aag gta caa gta ttt tga                        1665
Asp Val Asp Phe Leu Lys Val Gln Val Phe
545                 550

<210> SEQ ID NO 2
<211> LENGTH: 554
<212> TYPE: PRT
<213> ORGANISM: Saccharomyces cerevisiae

<400> SEQUENCE: 2

Met Thr Ala Lys Thr Phe Leu Leu Gln Ala Ser Ala Ser Arg Pro Arg
1               5                   10                  15

Ser Asn His Phe Lys Asn Glu His Asn Asn Ile Pro Leu Ala Pro Val
            20                  25                  30

Pro Ile Ala Pro Asn Thr Asn His His Asn Asn Ser Ser Leu Glu Phe
        35                  40                  45

Glu Asn Asp Gly Ser Lys Lys Lys Lys Ser Ser Leu Val Val Arg
    50                  55                  60

Thr Ser Lys His Trp Val Leu Pro Pro Arg Pro Arg Pro Gly Arg Arg
65                  70                  75                  80

Ser Ser Ser His Asn Thr Leu Pro Ala Asn Asn Thr Asn Asn Ile Leu
                85                  90                  95

Asn Val Gly Pro Asn Ser Arg Asn Ser Ser Asn Asn Asn Asn Asn
            100                 105                 110

Asn Ile Ile Ser Asn Arg Lys Gln Ala Ser Lys Glu Lys Arg Lys Ile
        115                 120                 125

Pro Arg His Ile Gln Thr Ile Asp Glu Lys Leu Ile Asn Asp Ser Asn
    130                 135                 140

Tyr Leu Ala Phe Leu Lys Phe Asp Asp Leu Glu Asn Glu Lys Phe His
145                 150                 155                 160

Ser Ser Ala Ser Ser Ile Ser Ser Pro Ser Tyr Ser Ser Pro Ser Phe
                165                 170                 175

Ser Ser Tyr Arg Asn Arg Lys Lys Ser Glu Phe Met Asp Asp Glu Ser
            180                 185                 190

Cys Thr Asp Val Glu Thr Ile Ala Ala His Asn Ser Leu Leu Thr Lys
        195                 200                 205

Asn His His Ile Asp Ser Ser Asn Val His Ala Pro Pro Thr Lys
    210                 215                 220
```

```
Lys Ser Lys Leu Asn Asp Phe Asp Leu Leu Ser Leu Ser Ser Thr Ser
225                 230                 235                 240

Ser Ser Ala Thr Pro Val Pro Gln Leu Thr Lys Asp Leu Asn Met Asn
                245                 250                 255

Leu Asn Phe His Lys Ile Pro His Lys Ala Ser Phe Pro Asp Ser Pro
            260                 265                 270

Ala Asp Phe Ser Pro Ala Asp Ser Val Ser Leu Ile Arg Asn His Ser
        275                 280                 285

Leu Pro Thr Asn Leu Gln Val Lys Asp Lys Ile Glu Asp Leu Asn Glu
    290                 295                 300

Ile Lys Phe Phe Asn Asp Phe Glu Lys Leu Glu Phe Phe Asn Lys Tyr
305                 310                 315                 320

Ala Lys Val Asn Thr Asn Asn Asp Val Asn Glu Asn Asn Asp Leu Trp
                325                 330                 335

Asn Ser Tyr Leu Gln Ser Met Asp Asp Thr Thr Gly Lys Asn Ser Gly
            340                 345                 350

Asn Tyr Gln Gln Val Asp Asn Asp Asn Met Ser Leu Leu Asn Leu
        355                 360                 365

Pro Ile Leu Glu Glu Thr Val Ser Ser Gly Asp Asp Lys Val Glu
    370                 375                 380

Pro Asp Glu Glu Asp Ile Trp Asn Tyr Leu Pro Ser Ser Ser Gln
385                 390                 395                 400

Gln Glu Asp Ser Ser Arg Ala Leu Lys Lys Asn Thr Asn Ser Glu Lys
                405                 410                 415

Ala Asn Ile Gln Ala Lys Asn Asp Glu Thr Tyr Leu Phe Leu Gln Asp
            420                 425                 430

Gln Asp Glu Ser Ala Asp Ser His His His Asp Glu Leu Gly Ser Glu
        435                 440                 445

Ile Thr Leu Ala Asp Asn Lys Phe Ser Tyr Leu Pro Pro Thr Leu Glu
    450                 455                 460

Glu Leu Met Glu Glu Gln Asp Cys Asn Asn Gly Arg Ser Phe Lys Asn
465                 470                 475                 480

Phe Met Phe Ser Asn Asp Thr Gly Ile Asp Gly Ser Ala Gly Thr Asp
                485                 490                 495

Asp Asp Tyr Thr Lys Val Leu Lys Ser Lys Lys Ile Ser Thr Ser Lys
            500                 505                 510

Ser Asn Ala Asn Leu Tyr Asp Leu Asn Asp Asn Asn Asn Asp Ala Thr
        515                 520                 525

Ala Thr Asn Glu Leu Asp Gln Ser Ser Phe Ile Asp Asp Leu Asp Glu
    530                 535                 540

Asp Val Asp Phe Leu Lys Val Gln Val Phe
545                 550

<210> SEQ ID NO 3
<211> LENGTH: 24
<212> TYPE: DNA
<213> ORGANISM: Artificial Sequence
<220> FEATURE:
<223> OTHER INFORMATION: synthetic DNA

<400> SEQUENCE: 3
gaaacagcta tgaccatgat tacg                                          24

<210> SEQ ID NO 4
<211> LENGTH: 35
<212> TYPE: DNA
<213> ORGANISM: Artificial Sequence
```

```
<220> FEATURE:
<223> OTHER INFORMATION: synthetic DNA

<400> SEQUENCE: 4
aagctcttaa aacgggaatt cccctaagaa accat                           35

<210> SEQ ID NO 5
<211> LENGTH: 35
<212> TYPE: DNA
<213> ORGANISM: Artificial Sequence
<220> FEATURE:
<223> OTHER INFORMATION: synthetic DNA

<400> SEQUENCE: 5
atggtttctt agggggaattc ccgttttaag agctt                          35

<210> SEQ ID NO 6
<211> LENGTH: 38
<212> TYPE: DNA
<213> ORGANISM: Artificial Sequence
<220> FEATURE:
<223> OTHER INFORMATION: synthetic DNA

<400> SEQUENCE: 6
gaccaagtta gctggtcgag ttcaagagaa aaaaaaag                        38

<210> SEQ ID NO 7
<211> LENGTH: 21
<212> TYPE: DNA
<213> ORGANISM: Artificial Sequence
<220> FEATURE:
<223> OTHER INFORMATION: synthetic DNA

<400> SEQUENCE: 7
ccagctaact tggtcgactt g                                          21

<210> SEQ ID NO 8
<211> LENGTH: 21
<212> TYPE: DNA
<213> ORGANISM: Artificial Sequence
<220> FEATURE:
<223> OTHER INFORMATION: synthetic DNA

<400> SEQUENCE: 8
gcgcgtaata cgactcacta t                                          21

<210> SEQ ID NO 9
<211> LENGTH: 22
<212> TYPE: DNA
<213> ORGANISM: Artificial Sequence
<220> FEATURE:
<223> OTHER INFORMATION: synthetic DNA

<400> SEQUENCE: 9
cctatctcta aacttcaaca cc                                         22

<210> SEQ ID NO 10
<211> LENGTH: 22
<212> TYPE: DNA
<213> ORGANISM: Artificial Sequence
<220> FEATURE:
<223> OTHER INFORMATION: synthetic DNA

<400> SEQUENCE: 10
tcagcaatag tggtcaacaa ct                                         22
```

```
<210> SEQ ID NO 11
<211> LENGTH: 20
<212> TYPE: DNA
<213> ORGANISM: Artificial Sequence
<220> FEATURE:
<223> OTHER INFORMATION: synthetic DNA

<400> SEQUENCE: 11
ttcgcatcta aggggtggtg                                              20

<210> SEQ ID NO 12
<211> LENGTH: 35
<212> TYPE: DNA
<213> ORGANISM: Artificial Sequence
<220> FEATURE:
<223> OTHER INFORMATION: synthetic DNA

<400> SEQUENCE: 12
gcgtgtacgc atgtaacttt gttcttcttg ttatt                             35

<210> SEQ ID NO 13
<211> LENGTH: 35
<212> TYPE: DNA
<213> ORGANISM: Artificial Sequence
<220> FEATURE:
<223> OTHER INFORMATION: synthetic DNA

<400> SEQUENCE: 13
ctaacattca acgctagacg gttctctaca attga                             35

<210> SEQ ID NO 14
<211> LENGTH: 23
<212> TYPE: DNA
<213> ORGANISM: Artificial Sequence
<220> FEATURE:
<223> OTHER INFORMATION: synthetic DNA

<400> SEQUENCE: 14
taagaaggca tgttggcctc tgt                                          23

<210> SEQ ID NO 15
<211> LENGTH: 35
<212> TYPE: DNA
<213> ORGANISM: Artificial Sequence
<220> FEATURE:
<223> OTHER INFORMATION: synthetic DNA

<400> SEQUENCE: 15
aataacaaga agaacaaagt tacatgcgta cacgc                             35

<210> SEQ ID NO 16
<211> LENGTH: 35
<212> TYPE: DNA
<213> ORGANISM: Artificial Sequence
<220> FEATURE:
<223> OTHER INFORMATION: synthetic DNA

<400> SEQUENCE: 16
tcaattgtag agaaccgtct agcgttgaat gttag                             35

<210> SEQ ID NO 17
<211> LENGTH: 18
<212> TYPE: DNA
<213> ORGANISM: Artificial Sequence
<220> FEATURE:
<223> OTHER INFORMATION: synthetic DNA

<400> SEQUENCE: 17
```

```
ggagacccac tgtacaac                                                      18

<210> SEQ ID NO 18
<211> LENGTH: 24
<212> TYPE: DNA
<213> ORGANISM: Artificial Sequence
<220> FEATURE:
<223> OTHER INFORMATION: synthetic DNA

<400> SEQUENCE: 18
gcagctgaaa gataataagg tatg                                               24

<210> SEQ ID NO 19
<211> LENGTH: 19
<212> TYPE: DNA
<213> ORGANISM: Artificial Sequence
<220> FEATURE:
<223> OTHER INFORMATION: synthetic DNA

<400> SEQUENCE: 19
ccttgatgcg tgcgtaacc                                                     19

<210> SEQ ID NO 20
<211> LENGTH: 40
<212> TYPE: DNA
<213> ORGANISM: Artificial Sequence
<220> FEATURE:
<223> OTHER INFORMATION: synthetic DNA

<400> SEQUENCE: 20
aaacgcgtgt acgcatgtaa tctcataaac ctatgcactg                              40

<210> SEQ ID NO 21
<211> LENGTH: 40
<212> TYPE: DNA
<213> ORGANISM: Artificial Sequence
<220> FEATURE:
<223> OTHER INFORMATION: synthetic DNA

<400> SEQUENCE: 21
tcatattcga cgatgtcgtc cgaactacag ttatcgcctc                              40

<210> SEQ ID NO 22
<211> LENGTH: 43
<212> TYPE: DNA
<213> ORGANISM: Artificial Sequence
<220> FEATURE:
<223> OTHER INFORMATION: synthetic DNA

<400> SEQUENCE: 22
cacacaaaca aacaaaacaa aatgaccgca aagactttc tac                           43

<210> SEQ ID NO 23
<211> LENGTH: 43
<212> TYPE: DNA
<213> ORGANISM: Artificial Sequence
<220> FEATURE:
<223> OTHER INFORMATION: synthetic DNA

<400> SEQUENCE: 23
```
gtagaaaagt ctttgcggtc attttgtttt gtttgtttgt gtg            43

<210> SEQ ID NO 24
<211> LENGTH: 35
<212> TYPE: DNA
<213> ORGANISM: Artificial Sequence
<220> FEATURE:
<223> OTHER INFORMATION: synthetic DNA

<400> SEQUENCE: 24
atatatctgc aggatccct tgacgggtat tctga                     35

<210> SEQ ID NO 25
<211> LENGTH: 35
<212> TYPE: DNA
<213> ORGANISM: Artificial Sequence
<220> FEATURE:
<223> OTHER INFORMATION: synthetic DNA

<400> SEQUENCE: 25
tcagaatacc cgtcaaggga tccctgcaga tatat                    35

<210> SEQ ID NO 26
<211> LENGTH: 22
<212> TYPE: DNA
<213> ORGANISM: Artificial Sequence
<220> FEATURE:
<223> OTHER INFORMATION: synthetic DNA

<400> SEQUENCE: 26
ccatattttc gttaggtcat tt                                  22

<210> SEQ ID NO 27
<211> LENGTH: 40
<212> TYPE: DNA
<213> ORGANISM: Artificial Sequence
<220> FEATURE:
<223> OTHER INFORMATION: synthetic DNA

<400> SEQUENCE: 27
cagtgcatag gtttatgaga ttacatgcgt acacgcgttt               40

<210> SEQ ID NO 28
<211> LENGTH: 40
<212> TYPE: DNA
<213> ORGANISM: Artificial Sequence
<220> FEATURE:
<223> OTHER INFORMATION: synthetic DNA

<400> SEQUENCE: 28
gaggcgataa ctgtagttcg gacgacatcg tcgaatatga               40

<210> SEQ ID NO 29
<211> LENGTH: 22
<212> TYPE: DNA
<213> ORGANISM: Artificial Sequence
<220> FEATURE:
<223> OTHER INFORMATION: synthetic DNA

<400> SEQUENCE: 29
accagcccat ctcaatccat ct                                  22

<210> SEQ ID NO 30
<211> LENGTH: 22
<212> TYPE: DNA
<213> ORGANISM: Artificial Sequence
<220> FEATURE:

<223> OTHER INFORMATION: synthetic DNA

<400> SEQUENCE: 30
agcgtatggg tgatgagagt ac                                          22

<210> SEQ ID NO 31
<211> LENGTH: 20
<212> TYPE: DNA
<213> ORGANISM: Artificial Sequence
<220> FEATURE:
<223> OTHER INFORMATION: synthetic DNA

<400> SEQUENCE: 31
gttgaagtcg cctggtagcc                                             20

<210> SEQ ID NO 32
<211> LENGTH: 20
<212> TYPE: DNA
<213> ORGANISM: Artificial Sequence
<220> FEATURE:
<223> OTHER INFORMATION: synthetic DNA

<400> SEQUENCE: 32
tgtccaggct acgtcgaatc                                             20

<210> SEQ ID NO 33
<211> LENGTH: 22
<212> TYPE: DNA
<213> ORGANISM: Artificial Sequence
<220> FEATURE:
<223> OTHER INFORMATION: synthetic DNA

<400> SEQUENCE: 33
ctcatacatg tttcatgagg gt                                          22

<210> SEQ ID NO 34
<211> LENGTH: 22
<212> TYPE: DNA
<213> ORGANISM: Artificial Sequence
<220> FEATURE:
<223> OTHER INFORMATION: synthetic DNA

<400> SEQUENCE: 34
acacccaatc tttcacccat ca                                          22

<210> SEQ ID NO 35
<211> LENGTH: 20
<212> TYPE: DNA
<213> ORGANISM: Artificial Sequence
<220> FEATURE:
<223> OTHER INFORMATION: synthetic DNA

<400> SEQUENCE: 35
ggaacccata gatgaagagg                                             20

<210> SEQ ID NO 36
<211> LENGTH: 20
<212> TYPE: DNA
<213> ORGANISM: Artificial Sequence
<220> FEATURE:
<223> OTHER INFORMATION: synthetic DNA

<400> SEQUENCE: 36
atccgctcta accgaaaagg                                             20

<210> SEQ ID NO 37

```
<211> LENGTH: 20
<212> TYPE: DNA
<213> ORGANISM: Artificial Sequence
<220> FEATURE:
<223> OTHER INFORMATION: synthetic DNA

<400> SEQUENCE: 37
tcctgcgcct gatacagaac                                                  20
```

YEAST MUTANT AND SUBSTANCE PRODUCTION METHOD USING THE SAME

CROSS-REFERENCE TO RELATED APPLICATIONS

This is a 371 National Stage Entry of PCT/JP2009/058078, filed Apr. 23, 2009, which claims priority from JP 2008-113053, filed Apr. 23, 2008.

TECHNICAL FIELD

The present invention relates to a yeast mutant obtained by modifying a wild-type yeast to constitutively express a certain gene and a substance production method using the same.

BACKGROUND ART

When a desired product is produced using yeast (*Saccharomyces cerevisiae*) or the like, a yeast mutant is prepared by gene introduction in a manner such that a gene involved in the biosynthesis of the desired product can be constitutively expressed in the yeast mutant, the yeast mutant is cultured under adequate culture conditions, and the desired product is collected inside or outside the cultured cells. In addition, when a desired product is a non-ethanol substance, it is preferable to reduce large amounts of produced ethanol. Hitherto, in order to reduce ethanol production capacity, gene disruptants from the pyruvate decarboxylase gene and the alcohol dehydrogenase gene involved in the ethanol production pathway have been prepared. However, particularly in the case of a bacterium exhibiting the Crabtree effect, such as *Saccharomyces cerevisiae*, proliferation or fermentation capacity significantly decreases while the amount of ethanol produced decreases, resulting in poor practical usefulness, which has been problematic (Non-Patent Document 1: Ishida, N. et al. (2006) Biosci. Biotechnol. Biochem., 70, pp. 1148-1153; Non-Patent Document 2: Flikweert, M. T. et al. (1996) Yeast 12, pp. 247-257; Non-Patent Document 3: Eri, A. et al. (1998) J. Ferment. Bioeng., 86, pp. 284-289; Patent Document 1: JP Patent Publication (Kohyo) No. 2003-500062 A; Patent Document 2: JP Patent Publication (Kohyo) No. 2001-516584 A; and Non-Patent Document 4: Skory, C. D. (2003) J. Ind. Microbiol. Biotechnol., 30, pp. 22-27). In addition, according to Non-Patent Documents 1, 3, and 4, ethanol can be significantly reduced by disrupting the genes involved in the ethanol production pathway. However, it is not always possible for the greatest portion of a product formed as a result of reduction of ethanol to be obtained in the form of a desired product.

Meanwhile, it has been reported that the yield of a desired product can be improved by partially blocking the ethanol production pathway so as to promote the metabolic pathway of the desired product (Non-Patent Document 5: Saitoh, S (2005) Appl. Environ. Microbiol., 71, pp. 2789-2792). However, in such case, although the yield of the desired product can be improved, ethanol reduction is insufficient and the fermentation rate decreases slightly, which is problematic.

Patent Document 1: JP Patent Publication (Kohyo) No. 2003-500062 A
Patent Document 1: JP Patent Publication (Kohyo) No. 2001-516584 A
Non-Patent Document 1: Ishida, N. et al. (2006) Biosci. Biotechnol. Biochem., 70, pp. 1148-1153
Non-Patent Document 2: Flikweert, M. T. et al. (1996) Yeast 12, pp. 247-257
Non-Patent Document 3: Eri, A. et al. (1998) J. Ferment. Bioeng., 86, pp. 284-289
Non-Patent Document 4: Skory, C. D. (2003) J. Ind. Microbiol. Biotechnol., 30, pp. 22-27
Non-Patent Document 5: Saitoh, S (2005) Appl. Environ. Microbiol., 71, pp. 2789-2792

DISCLOSURE OF THE INVENTION

Problem to be Solved by the Invention

Therefore, in view of the above circumstances, it is an object of the present invention to provide a yeast mutant capable of having the significantly improved ability to produce a desired product and maintaining its growth rate and fermentation rate at excellent levels for the production of the desired product with the use of yeast and to provide a substance production method using the same.

Means for Solving Problem

As a result of intensive studies in order to attain the above object, the present inventors have found that a yeast into which a gene involved in the production of a desired product has been introduced and allowed to constitutively express the HAP4 gene can have the significantly improved ability to produce the desired product while maintaining its growth rate and fermentation rate. This has led to the completion of the present invention.

The present invention encompasses the following (1) and (2).

(1) A yeast mutant into which a foreign gene that encodes an enzyme involved in the production of a desired product and the HAP4 gene that can be constitutively expressed or a homologous gene thereof have been introduced.

Preferably, the yeast mutant (1) above is a mutant strain having alcohol productivity lower than that of a wild-type yeast. For instance, the alcohol productivity can be lowered by reducing the enzyme activity of an enzyme involved in alcohol synthesis. Herein, examples of an enzyme involved in alcohol synthesis include pyruvate decarboxylase and/or alcohol dehydrogenase. An example of pyruvate decarboxylase described above can be an enzyme encoded by at least one gene selected from the group consisting of the PDC1 gene, the PDC5 gene, and the PDC6 gene. An example of the alcohol dehydrogenase described above can be an enzyme encoded by the ADH1 gene. In addition, a yeast belonging to the genus *Saccharomyces*, and particularly preferably, a yeast from a strain of *Saccharomyces cerevisiae*, is used as the yeast mutant (1) above. In addition, an example of the above foreign gene can be a gene encoding a protein having lactate dehydrogenase activity.

(2) A substance production method using yeast, comprising the steps of: culturing the aforementioned yeast mutant of the present invention, producing a desired product inside and/or outside the cultured cells, and collecting the desired product.

In the substance production method (2) above, a desired product may be an organic acid. In addition, a desired product is particularly preferably lactic acid. Alternatively, a desired product may be a non-ethanol alcohol.

Effects of the Invention

According to the present invention, a yeast mutant capable of having the excellent ability to produce a desired product while maintaining its growth rate and fermentation rate at excellent levels can be provided. In addition, a desired product can be produced at low cost with the use of the yeast mutant of the present invention.

This description includes part or all of the contents as disclosed in the description and/or drawings of Japanese Patent Application No. 2008-113053, which is a priority document of the present application.

BEST MODE FOR CARRYING OUT THE INVENTION

Figure 1:
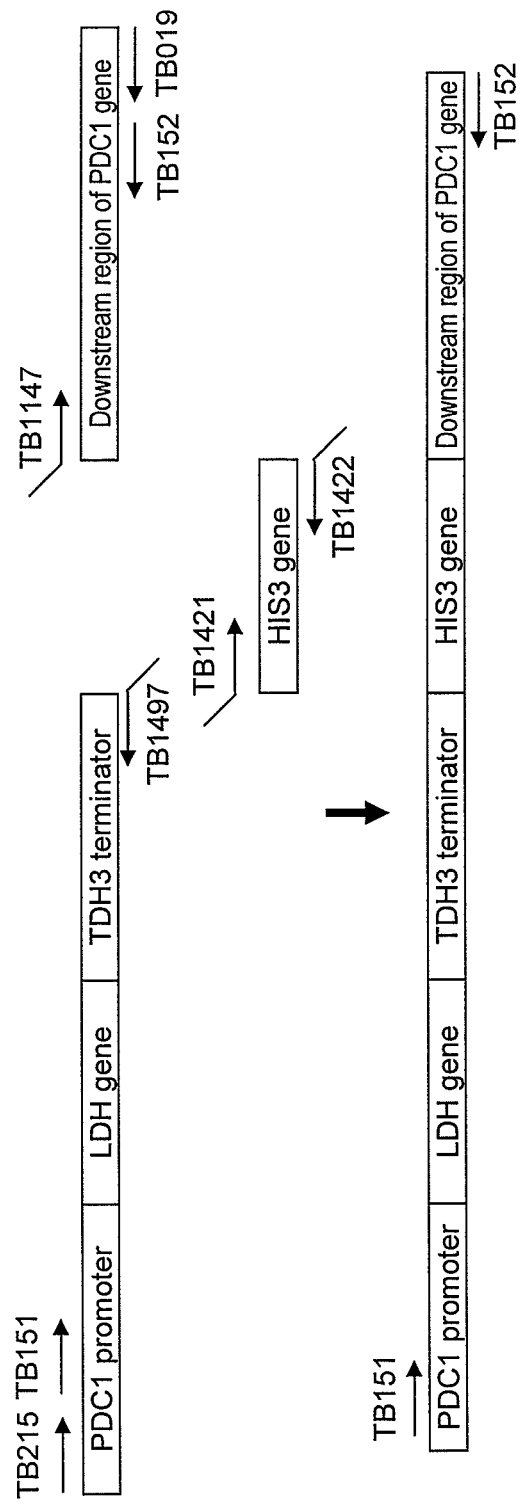
FIG. 1 schematically shows the flow of the construction of a DNA fragment for LDH gene introduction/PDC1 gene disruption.

Hereinafter, the present invention is described in detail.

The yeast mutant of the present invention is a yeast mutant into which a foreign gene that encodes an enzyme involved in the production of a desired product and the HAP4 gene that can be constitutively expressed or a homologous gene thereof have been introduced. Herein, the HAP4 gene encodes an HAP4 protein constituting a subunit of an Hap2p/3p/4p/5p CCAAT-bonded complex that is hemiactivated or glucose-repressed. This complex is known to exhibit transactivation activities of a variety of genes. In particular, the HAP4 protein and the above complex are described in detail in Gancedo J M (1998) Yeast carbon catabolite repression, Microbiol. Mol. Biol. Rev., 62(2), pp. 334-361.

The nucleotide sequence of a coding region in the HAP4 gene and the amino acid sequence of the HAP4 protein are shown in SEQ ID NOS: 1 and 2, respectively. In addition, the HAP4 gene that is introduced so as to be constitutively expressed is not limited to a gene encoding a protein containing the amino acid sequence shown in SEQ ID NO: 2. It may be a gene encoding a protein containing an amino acid sequence having, for example, 70% or more, preferably 80% or more, more preferably 90% or more, further preferably 95% or more, and most preferably 97% or more identity to the amino acid sequence shown in SEQ ID NO: 2 and constituting the above complex so as to exhibit transactivation activity. Herein, the term "identity" refers to the value obtained in the default setting with the use of a computer program implemented with the BLAST algorithm and a database containing gene sequence information.

In addition, the HAP4 gene may be a gene encoding a protein containing an amino acid sequence derived from the amino acid sequence shown in SEQ ID NO: 2 by deletion, substitution, addition, or insertion of 1 or more amino acid(s) (e.g., 2 to 60, preferably 2 to 50, more preferably 2 to 40, further preferably 2 to 30, and most preferably 2 to 15 amino acids) and constituting the above complex so as to exhibit transactivation activity.

Further, examples of the HAP4 gene are not limited to a gene containing the nucleotide sequence shown in SEQ ID NO: 1 and may include a gene that hybridizes to the entirety of or a portion (consisting of consecutive nucleotides) of a polynucleotide having a nucleotide sequence complementary to the nucleotide sequence shown in SEQ ID NO: 1 under stringent conditions and encodes a protein constituting the above complex so as to exhibit transactivation activity. Herein, the term "under stringent conditions" refers to what are called conditions that cause formation of a specific hybrid but not a non-specific hybrid. For instance, conditions of hybridization with 6×SSC (sodium chloride/sodium citrate) at 45° C. and subsequent washing with 0.2 to 1×SSC and 0.1% SDS at 50° C. to 65° C. can be referred to. Alternatively, conditions of hybridization with 1×SSC at 65° C. to 70° C. and subsequent washing with 0.3×SSC at 65° C. to 70° C. can be referred to as such conditions. Hybridization can be carried out by a conventionally known method such as the method described in J. Sambrook et al. Molecular Cloning, A Laboratory Manual, 2nd Ed., Cold Spring Harbor Laboratory (1989).

In addition, the aforementioned amino acid sequence having a certain sequence identity, an amino acid sequence with deletion, substitution, or addition of amino acid(s), or the like can be obtained by modifying a polynucleotide having a nucleotide sequence (e.g., the nucleotide sequence shown in SEQ ID NO: 1) that encodes a protein containing the amino acid sequence shown in SEQ ID NO: 2 by a method known in the art. Also, a polynucleotide that hybridizes to the entirety of or a portion (consisting of consecutive nucleotides) of a polynucleotide having a nucleotide sequence complementary to the nucleotide sequence shown in SEQ ID NO: 1 under stringent conditions can be obtained by modifying a polynucleotide having the nucleotide sequence shown in SEQ ID NO: 1 in a similar manner by a method known in the art. Mutagenesis in a nucleotide sequence can be caused by a known method such as the Kunkel method, the gapped duplex method, or a method similar to such a known method. For instance, mutagenesis can be caused with the use of a mutagenesis kit (e.g., Mutant-K or Mutant-G (product name, TAKARA Bio)) based on a site-directed mutagenesis method, an LA PCR in vitro Mutagenesis series kit (product name, TAKARA Bio), or the like. Alternatively, a mutagenesis method may be a method using a chemical mutagen represented by EMS (ethyl methanesulfonate), 5-bromouracil, 2-aminopurine, hydroxylamine, N-methyl-N'-nitro-N-nitrosoguanidine, or a different carcinogenic compound, a method comprising radiation treatment using radioactive rays such as X-rays, γ-rays, β-rays, γ-rays, or an ion beam, or a method comprising ultraviolet treatment.

Further, it is possible to confirm whether an arbitrary protein can constitute the above complex so as to exhibit transactivation activity with the use of, for example, an experimental system disclosed in David S. McNabb et al., Eukaryotic Cell, November 2005, pp. 1829-1839, Vol. 4, No. 11. Specifically, this reference describes that when an Hap2p/Hap3p/Hap5p heterotrimer is constructed and the Hap4 protein is allowed to act on the construct, the protein constitutes the complex described above so as to exhibit transactivation activity. Therefore, it is readily possible to examine whether or not an arbitrary protein has functions similar to those of the HAP4 protein with the use of the experimental system described in the reference.

As an aside, the HAP4 gene can be isolated from *Saccharomyces cerevisiae* by a conventionally known method so as to be used. In addition, in the present invention, it is also possible to use a homologous gene of the HAP4 gene, instead of the HAP4 gene. Examples of a homologous gene of the HAP4 gene include a *Kluyveromyces lactis*-derived HAP4 homologous gene (see Bourgarel, D. et al., 1999. Mol. Microbiol. 31:1205-1215) and a *Hansenula polymorpha*-derived HAP4 homologous gene (see Sybirna, K. et al., 2005. Curr. Genet. 47:172-181). The nucleotide sequences of these HAP4 homologous genes and the amino acid sequences of HAP4 homologous proteins encoded by such genes can be obtained from a known database such as Genbank.

For example, in order to cause the HAP4 gene or a homologous gene thereof described above to be constitutively expressed in a host, a method using a promoter for constitutive expression can be used. Specifically, a method comprising constructing an expression vector in which the HAP4 gene or a homologous gene thereof is arranged under the regulation of a promoter for constitutive expression and transforming a host with the expression vector can be used. Herein, the term "promoter for constitutive expression" refers to a promoter having a function to cause the expression of a downstream gene regardless of growth conditions for a host cell. A promoter for constitutive expression can be used without particular limitation, and thus it may be adequately selected depending on type of host cell or gene to be regulated. Examples of a promoter for constitutive expression for *Saccharomyces cerevisiae* include an ADH1 promoter, an HIS3 promoter, a TDH3 promoter, a CYC3 promoter, a CUP1 promoter, and an HOR7 promoter.

In addition, the promoter for constitutive expression and the expression vector containing the HAP4 gene or a homologous gene thereof described above may have other sequences that control the expression of the HAP4 gene or a homologous gene thereof upon introduction into the host. Specific examples are an operator, an enhancer, a silencer, a ribosome binding sequence, a terminator, and the like.

Herein, a host subjected to gene introduction for the constitutive expression of the HAP4 gene or a homologous gene thereof is not particularly limited as long as it is a yeast. Examples of yeasts that can be used as hosts include ascomycetous yeast of *Ascomycotina* (*Ascomycota*), basidiomycetous yeast of *Basidiomycotina* (*Basidiomycota*), and deuteromycetous yeast of *Deuteromycetes* (Fungi Imperfecti) (*Deuteromycota*). Preferably, ascomycetous yeast, and particularly preferably, *Saccharomyces cerevisiae, Candida utilis, Pichia pastris*, or the like, which is a budding yeast, or *Shizosaccharomyces pombe* or the like, which is a fission yeast, can be used. In addition, *Kluyveromyces lactis* and *Hansenula polymorpha* can be used as hosts.

In addition, it is particularly preferable to use, as a yeast serving as a host, a mutant strain having lowered alcohol productivity. Herein, the expression "lowered alcohol productivity" indicates alcohol productivity significantly lower than that of a wild-type yeast. For example, alcohol productivity can be lowered by introducing a mutation into a wild-type yeast so as to reduce enzyme activity of an enzyme involved in alcohol synthesis. Examples of enzymes involved in alcohol synthesis include pyruvate decarboxylase and alcohol dehydrogenase. Alcohol productivity can be lowered by reducing the enzyme activity of either or both pyruvate decarboxylase and alcohol dehydrogenase. Examples of a gene encoding *Saccharomyces cerevisiae*-derived pyruvate decarboxylase include the PDC1 gene, the PDC5 gene, and the PDC6 gene. Examples of a gene encoding *Saccharomyces cerevisiae*-derived alcohol dehydrogenase include the ADH1 gene.

Alcohol productivity can be lowered by deficiency of a single gene or a plurality of genes selected from among the genes described above. Herein, methods of deficiency of genes are not particularly limited. However, examples thereof include a method comprising deleting the gene, a method comprising introducing a mutation into the gene so as to cause the expression of an inactive enzyme, and a method comprising deleting or mutating the expression control region (e.g., promoter) of the gene. In addition, examples of a method of deficiency of genes include a method comprising causing the expression of siRNA (small interfering RNA), antisense RNA, and ribozymes of the gene in a host cell.

In addition, the yeast mutant of the present invention has a foreign gene that encodes an enzyme involved in the production of a desired product, and thus it can be used for the production of the desired product. Such desired product is not particularly limited as long as it is a substance that can be biosynthesized in a yeast. Examples thereof include: organic acids such as lactic acid, acrylic acid, acetic acid, pyruvic acid, 3-hydroxypropionic acid, fumaric acid, succinic acid, itaconic acid, levulinic acid, adipic acid, ascorbic acid, and citric acid; and alcohols such as 1-propanol, 2-propanol, 1-butanol, isobutanol, 2-methyl-1-butanol, and 3-methyl-1-butanol.

In particular, in a case in which a desired product is lactic acid, an example of a foreign gene is a lactate dehydrogenase (LDH) gene involved in lactic acid synthesis. In other words, lactic acid production capacity can be imparted to a yeast mutant by introducing the LDH gene serving as a foreign gene into the mutant. There exist a variety of LDH homologs in vivo, and LDH homologs differ in accordance with organism type. LDH used in the present invention includes LDH that is artificially synthesized via chemical synthesis or genetic engineering, in addition to naturally-derived LDH. Preferably, LDH is derived from a prokaryote such as *Lactobacillus helveticus, Lactobacillus casei, Kluyveromyces thermotolerans, Torulaspora delbrueckii, Schizosaccharomyces pombe*, or *Rhizopus oryzae*, or it is derived from a eukaryote such as mold. More preferably, LDH is derived from a higher eukaryote such as a plant, animal, or insect. For example, bovine-derived LDH (L-LDH) is preferably used. The aforementioned genes are introduced into yeast so that lactic acid production capacity can be imparted to the microorganism.

In addition, the above foreign gene may be introduced under the regulation of a constitutive promoter or may be introduced under the regulation of an inducible promoter. Further, the above foreign gene does not need to be introduced under the regulation of a promoter containing the CCAAT consensus sequence to which the Hap2p/3p/4p/5p CCAAT-bonded complex (capable of recognizing the sequence) binds.

The yeast mutant of the present invention constitutively expresses the HAP4 gene or a homologous gene thereof. Therefore, the productivity of a desired product can be significantly improved. In particular, the HAP4 gene or a homologous gene thereof is constitutively expressed in a yeast mutant having lowered alcohol productivity such that the productivity of the desired product can be improved without reduction in the growth rate and the fermentation rate of yeast. With the use of the yeast mutant of the present invention as described above, the yield of the desired product can be significantly improved. Accordingly, the production cost of the desired product can be significantly reduced.

EXAMPLES

The present invention is hereafter described in greater detail with reference to the following examples, although the technical scope of the present invention is not limited thereto.

Example 1

Preparation of DNA Fragment for LDH Gene Introduction/PDC1 Gene Disruption

First, the lactate dehydrogenase (LDH) gene serving as a foreign gene was introduced into yeast serving as a host. In addition, a DNA fragment for disruption of the pyruvate synthase gene (PDC1 gene) involved in alcohol synthesis was prepared.

Specifically, a DNA fragment obtained by fusing a PDC1 promoter, the LDH gene, and a TDH3 terminator was amplified by PCR with the use of plasmid pBTrp-PDC1-LDHKCB disclosed in JP Patent Publication (Kokai) No. 2003-259878 A as a template. In this case, TB215 (5'-GAAACAGCTATGACCATGATTACG-3'; SEQ ID NO: 3) and TB1497 (5'-AAGCTCTTAAAACGGGAATTCCCCTAAGAAACCAT-3'; SEQ ID NO: 4) were used as primers for PCR (see FIG. 1).

Meanwhile, the HIS3 gene was amplified using plasmid pRS403 (obtainable from ATCC) as a template. In this case, TB1421 (5'-ATGGTTTCTTAGGGGAATTCCCGTTTTAAGAGCTT-3'; SEQ ID NO: 5) and TB1422 (5'-GACCAAGTTAGCTGGTCGAGTTCAA-GAGAAAAAAAAAG-3'; SEQ ID NO: 6) were used as primers for PCR.

In addition, a DNA fragment in the downstream region of the PDC1 gene was amplified by PCR with the use of the above pBTrp-PDC1-LDHKCB as a template. In this case, TB1147 (5'-CCAGCTAACTTGGTCGACTTG-3; SEQ ID NO: 7) and TB019 (5'-GCGCGTAATACGACTCACTAT-3; SEQ ID NO: 8) were used as primers for PCR.

The three types of PCR products amplified above were used as templates and combined in series according to the method of Shevchuk, N. A. et al. (Shevchuk, N. A. et al. (2004), Construction of long DNA molecules using long PCR-based fusion of several fragments simultaneously, Nucleic Acids Research 32(2) e19). In this case, TB151 (5'-CCTATCTCTAAACTTCAACACC-3'; SEQ ID NO: 9) and TB152 (5'-TCAGCAATAGTGGTCAACAACT-3'; SEQ ID NO: 10) were used as primers. In addition, the obtained DNA fragment was found to contain a region in which a PDC1 promoter, the LDH gene, and a TDH3 terminator were fused in such order, the LEU2 gene serving as a selection marker, and the downstream region of the PDC1 gene serving as a recombination region. Hereinafter, this DNA fragment is referred to as a "DNA fragment for LDH gene introduction/PDC1 gene disruption."

Preparation of DNA Fragment for PDC5 Gene Disruption

Figure 2:
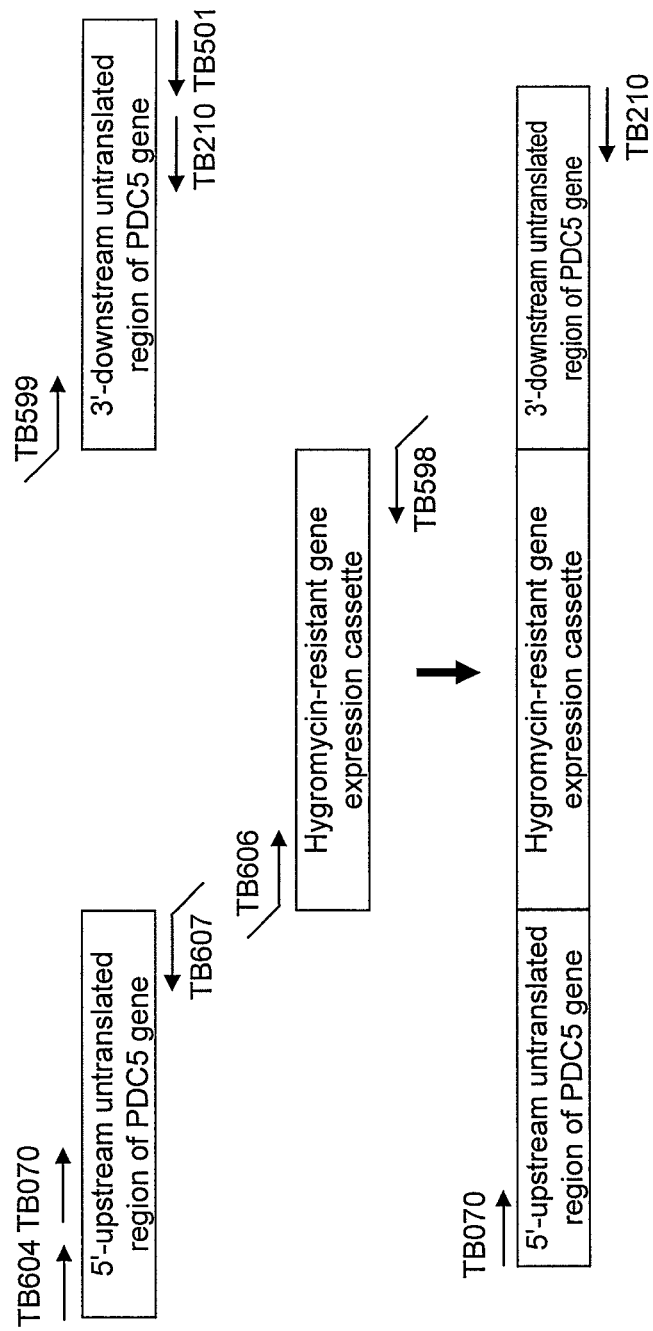
FIG. 2 schematically shows the flow of the construction of a DNA fragment for PDC5 gene disruption.

Also, in this Example, a DNA fragment for PDC5 gene disruption was prepared. Specifically, a DNA fragment of the 5'-upstream untranslated region and a DNA fragment of the 3'-downstream untranslated region of the PDC5 gene were separately amplified by PCR with the use of genomic DNA of the *Saccharomyces cerevisiae* BY4742 strain (Invitrogen) as a template (see FIG. 2). PCR primers used herein were TB604 (5'-TTCGCATCTAAGGGGTGGTG-3'; SEQ ID NO: 11) and TB607 (5'-GCGTGTACGCATGTAACTTTGTTCTTCTTGTTATT-3'; SEQ ID NO: 12) for the former and TB599 (5'-CTAACATTCAACGCTAGACGGTTCTCTACAATTGA-3'; SEQ ID NO: 13) and TB501 (5'-TAAGAAGGCATGTTGGCCTCTGT-3'; SEQ ID NO: 14) for the latter.

In addition, an expression cassette of a hygromycin-resistant gene was amplified by PCR with the use of, as a template, plasmid pBHPH-PT disclosed in JP Patent Publication (Kokai) No. 2003-259878 A. PCR primers used herein were TB606 (5'-AATAACAAGAAGAACAAAGTTACATGCG-TACACGC-3'; SEQ ID NO: 15) and TB598 (5'-TCAATTG-TAGAGAACCGTCTAGCGTTGAATGTTAG-3'; SEQ ID NO: 16).

The three types of PCR products amplified above were used as templates and combined in series according to the method of Shevchuk, N. A. et al. In this case, TB070 (5'-GGAGACCCACTGTACAAC-3'; SEQ ID NO: 17) and TB210 (5'-GCAGCTGAAAGATAATAAGGTATG-3'; SEQ ID NO: 18) were used as primers for PCR. Hereinafter, this DNA fragment is referred to as a "DNA fragment for PDC5 gene disruption."

Preparation of DNA Fragment for HAP4 Gene Overexpression

Figure 3:
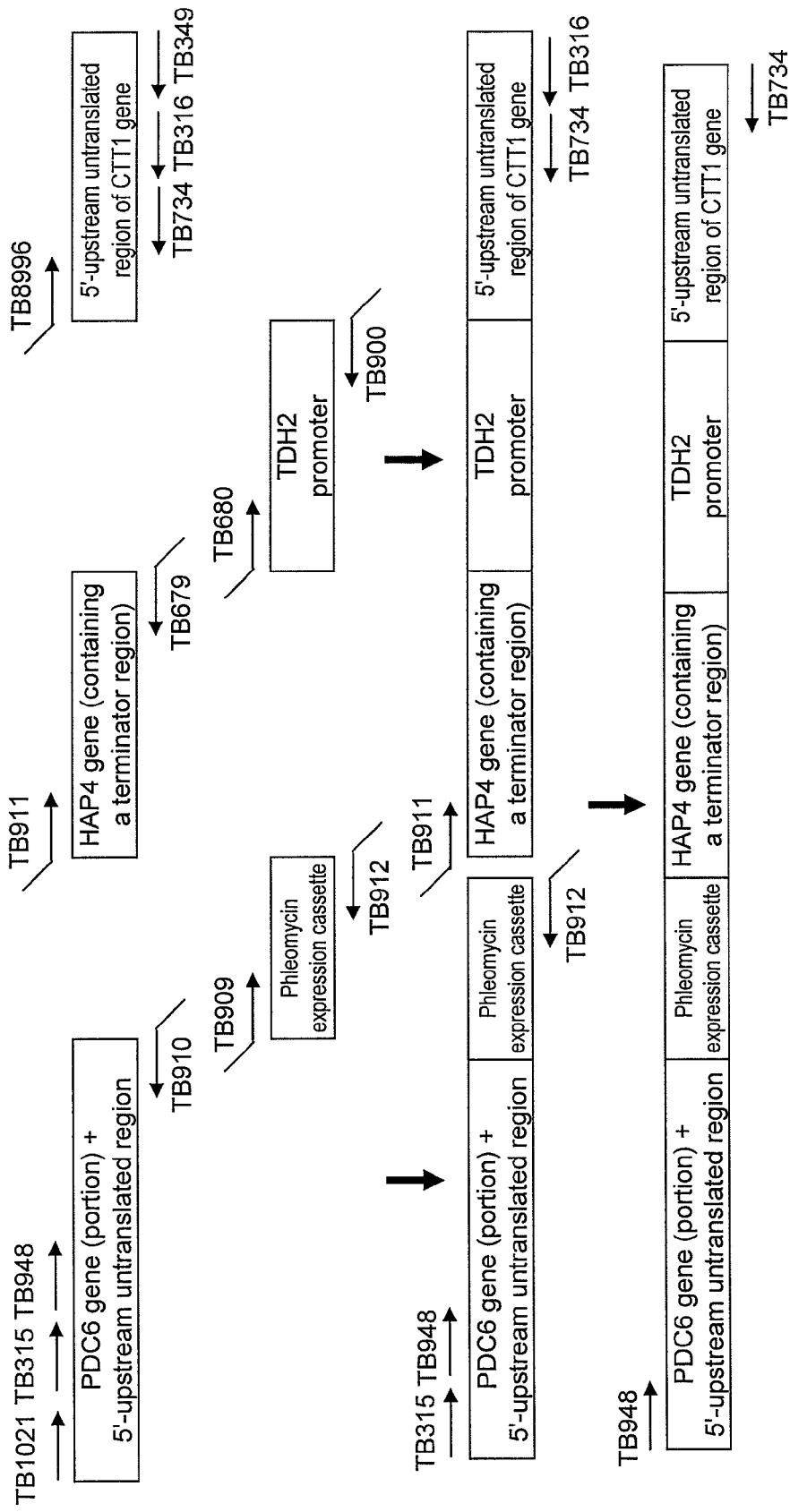
FIG. 3 schematically shows the flow of the construction of a DNA fragment for HAP4 gene overexpression.

Also, in this Example, a DNA fragment for the overexpression of the *Saccharomyces cerevisiae*-derived HAP4 gene was prepared. Specifically, a DNA fragment containing a portion of the PDC6 gene and the 5'-upstream untranslated region of the gene, a DNA fragment containing the HAP4 gene and the terminator region of the gene, a DNA fragment containing the TDH2 promoter region, and a DNA fragment containing the 5'-upstream untranslated region of the CTT1 gene were amplified by PCR with the use of genomic DNA of the *Saccharomyces cerevisiae* BY4742 strain as a template (see FIG. 3). Herein, the following PCR primers were used respectively, for the fragments: TB1021 (5'-CCTTGAT-GCGTGCGTAACC-3'; SEQ ID NO: 19) and TB910 (5'-AAACGCGTGTACGCATGTAATCTCAT-AAACCTATGCACTG-3'; SEQ ID NO: 20); TB911 (5'-TCATATTCGACGATGTCGTCCGAACTACAGTTATC-GCCTC-3'; SEQ ID NO: 21) and TB679 (5'-CACACAAA-CAAACAAAACAAAATGACCGCAAAGACTTTTCTAC-3; SEQ ID NO: 22); TB680 (5'-GTAGAAAAGTCTTTGCG-GTCATTTTGTTTTGTTTGTTTGTGTG-3'; SEQ ID NO: 23) and TB900 (5'-ATATATCTGCAGGGATCCCT-TGACGGGTATTCTGA-3'; SEQ ID NO: 24); and TB8996 (5'-TCAGAATACCCGTCAAGGGATCCCTGCA-GATATAT-3'; SEQ ID NO: 25) and TB349 (5'-CCATATTTTCGTTAGGTCATTT-3'; SEQ ID NO: 26).

In addition, a phleomycin expression cassette was amplified by PCR with the use of, as a template, plasmid pBble-LDHKCB disclosed in JP Patent Publication (Kokai) No. 2003-259878 A. PCR primers used herein were TB909 (5'-CAGTGCATAGGTTTATGAGATTACAT-GCGTACACGCGTTT-3'; SEQ ID NO: 27) and TB912 (5'-GAGGCGATAACTGTAGTTCGGACGACATCGTCGA-ATATGA-3'; SEQ ID NO: 28).

The PCR product containing a portion of the PDC6 gene and the 5'-upstream untranslated region of the gene and the phleomycin expression cassette amplified above were used as templates and bound to each other by PCR according to the aforementioned method of Shevchuk, N. A., et al. PCR primers used herein were TB315 (5'-ACCAGCCCATCTCAATC-CATCT-3'; SEQ ID NO: 29) and TB912. In addition, the PCR product containing the HAP4 gene and the terminator region of the gene, the PCR product containing the TDH2 promoter region, and the PCR product containing the 5'-upstream untranslated region of the CTT1 gene amplified above were used as templates and combined in series by PCR in a similar manner. Herein, PCR primers used were TB911 and TB316 (5'-AGCGTATGGGTGATGAGAGTAC-3'; SEQ ID NO: 30).

Then, the two fragments obtained by binding as described above were further bound to each other by PCR in a similar manner with the use of DNAs as templates. In this case, TB948 (5'-GTTGAAGTCGCCTGGTAGCC-3; SEQ ID NO: 31) and TB734 (5'-TGTCCAGGCTACGTCGAATC-3'; SEQ ID NO: 32) were used as primers for PCR. The eventually obtained DNA fragment is referred to as a "DNA fragment for HAP4 gene overexpression."

Preparation of the LDH Gene-Introduced/PDC1 Gene-Disrupted Cell Line

With the use of a Frozen-EZ Yeast Transformation II kit (ZYMO RESEARCH), transformation was carried out by introducing the above DNA fragment for LDH gene introduction/PDC1 gene disruption into the BY4742 strain. In this case, transformation was carried out according to the protocols included with the kit. After transformation, the resultant was applied to a leucine selection medium (SD-Leu) on a plate, followed by culture at 30° C. for 3 days. Thereafter, a transformant was selected. Genomic DNA was prepared from the transformant. It was confirmed by PCR that the DNA fragment for LDH gene introduction/PDC1 gene disruption had been incorporated into the chromosome. For PCR in this case, TB324 (5'-CTCATACATGTTTCATGAGGGT-3'; SEQ ID NO: 33) and TB304 (5'-ACACCCAATCTTTCAC-CCATCA-3; SEQ ID NO: 34) were used as primers located on the exterior side of the DNA fragment for LDH gene introduction/PDC1 gene disruption. As a result, it was confirmed that the LDH gene was incorporated into the chromosome, resulting in disruption of the PDC1 gene in the BY4742 strain. Hereinafter, this transformed yeast is referred to as "LDH gene-introduced/PDC1 gene-disrupted cell line."

Preparation of LDH Gene-Introduced/PDC1 Gene-Disrupted and PDC5 Gene-Disrupted Cell Line Next, the LDH gene-introduced/PDC1 gene-disrupted cell line was transformed with the use of the DNA fragment for PDC5 gene disruption. In addition, the above transformation method was used. After transformation, the resultant was applied to a YPD medium containing 200 µg/ml hygromycin on a plate, followed by culture at 30° C. for 3 days. Thereafter, a transformant was selected. Genomic DNA was prepared from the transformant. Then, it was confirmed by PCR that the DNA fragment for PDC5 gene disruption was incorporated into the chromosome. For PCR in this case, TB077 (5'-GGAACCCATAGATGAAGAGG-3'; SEQ ID NO: 35) and TB434 (5'-ATCCGCTCTAACCGAAAAGG-3'; SEQ ID NO: 36) were used as a primer located on the exterior side of the DNA fragment for PDC5 gene disruption and a primer located on the interior side of the DNA fragment for PDC5 gene disruption, respectively. As a result, it was confirmed that the PDC5 gene was disrupted in the LDH gene-introduced/PDC1 gene-disrupted cell line. Hereinafter, the transformed yeast is referred to as "LDH gene introduced/PDC1 gene-disrupted and PDC5 gene-disrupted cell line."

Preparation of HAP4 Gene-Introduced Cell Line

Next, the above LDH gene-introduced/PDC 1 gene-disrupted cell line and the LDH gene-transrected/PDC1 gene-disrupted and PDC5 gene-disrupted cell line were transformed with the use of the aforementioned DNA fragment for HAP4 gene overexpression. In addition, the above transformation method was used. After transformation, the resultant was applied to a YPD medium containing 100 µg/ml phleomycin on a plate, followed by culture at 30° C. for 3 to 5 days.

Thereafter, a transformant was selected. Genomic DNA was prepared from the transformant. Then, it was confirmed by PCR that the DNA fragment for HAP4 gene overexpression was incorporated into the chromosome. For PCR in this case, TB315 and TB1020 (5'-TCCTGCGCCTGATACAGAAC-3'; SEQ ID NO: 37) were used as a primer located on the exterior side of the DNA fragment for HAP4 gene overexpression and a primer located on the interior side of the DNA fragment for HAP4 gene overexpression, respectively. As a result, it was confirmed that the DNA fragment for HAP4 gene overexpression was introduced into the chromosome of the LDH gene-introduced/PDC1 gene-disrupted cell line and that of the LDH gene-introduced/PDC1 gene-disrupted and PDC5 gene-disrupted cell line.

Proliferation Test

The relative proliferation rate was calculated for the above prepared LDH gene-introduced/PDC1 gene-disrupted cell line (HAP4 non-introduced cell line in this test) and the LDH gene-introduced/PDC1 gene-disrupted cell line that had been introduced with the DNA fragment for HAP4 gene overexpression (HAP4-introduced cell line in this test). Specifically, each test cell line was inoculated into 100 ml of a YPD (yeast extract (1%), peptone (2%), and glucose (2%)) liquid medium dispensed into a 500-ml baffled Erlenmeyer flask, followed by shake culture at 30° C. at 120 rpm (amplitude: 35 mm) for 15 to 20 hours. Thereafter, cells were harvested at a cell concentration of 0.7% to 1.0%. The test strain at a cell concentration of 0.01% was inoculated again under the same conditions. Sampling was performed approximately every 2 hours after the onset of proliferation, followed by cell concentration determination. The relative proliferation rate was calculated by the following equation, provided that cells were confirmed to be in the logarithmic growth phase during the period from 2 to 10 hours after the onset of proliferation.

$$\text{Relative proliferation rate } [h^{-1}] = \frac{\ln 2}{\text{Cell doubling time}} = \frac{\ln\left(\frac{\text{Cell concentration 10 hours after the onset of proliferation}}{\text{Cell concentration 2 hours after the onset of proliferation}}\right)}{10 - 2} \quad \text{[Equation 1]}$$

Table 1 shows results of the proliferation test. As shown in table 1, in the case of the HAP4-introduced cell line, the proliferation rate was substantially comparable to that of the HAP4 non-introduced cell line.

TABLE 1

|  | HAP4 non-introduced cell line | HAP4-introduced cell line |
| --- | --- | --- |
| Relative proliferation rate [h$^{-1}$] | 0.45 | 0.44 |

Fermentation Test 1

The above prepared LDH gene-introduced/PDC 1 gene-disrupted cell line (HAP4 non-introduced cell line in this test) and the LDH gene-introduced/PDC1 gene-disrupted cell line that had been introduced with the DNA fragment for HAP4 gene overexpression (HAP4-introduced cell line in this test) were subjected to a fermentation test. Specifically, each test cell line was inoculated into a YPD medium (yeast extract (1%), peptone (2%), and glucose (2%)), followed by culture at 30° C. for 24 hours. After culture, cells were collected via centrifugation (2000 g, 3 minutes).

Next, a fermentation medium (25 ml; glucose (11%), yeast extract (1%), and calcium carbonate (4%)) was placed in a 50-ml flask. The cells were applied to the medium so as to result in a cell concentration of 0.5%, followed by fermentation at 80 rpm/minute (shaking amplitude: 40 mm) at 34° C. for 2 to 3 days. After fermentation, the amounts of produced lactic acid and ethanol were examined. In addition, the lactic acid yield was calculated by the following equation.

Lactic acid yield(%)=Maximum lactic acid concentration(%)/Added sugar concentration(%)  (10)

Figure 4:
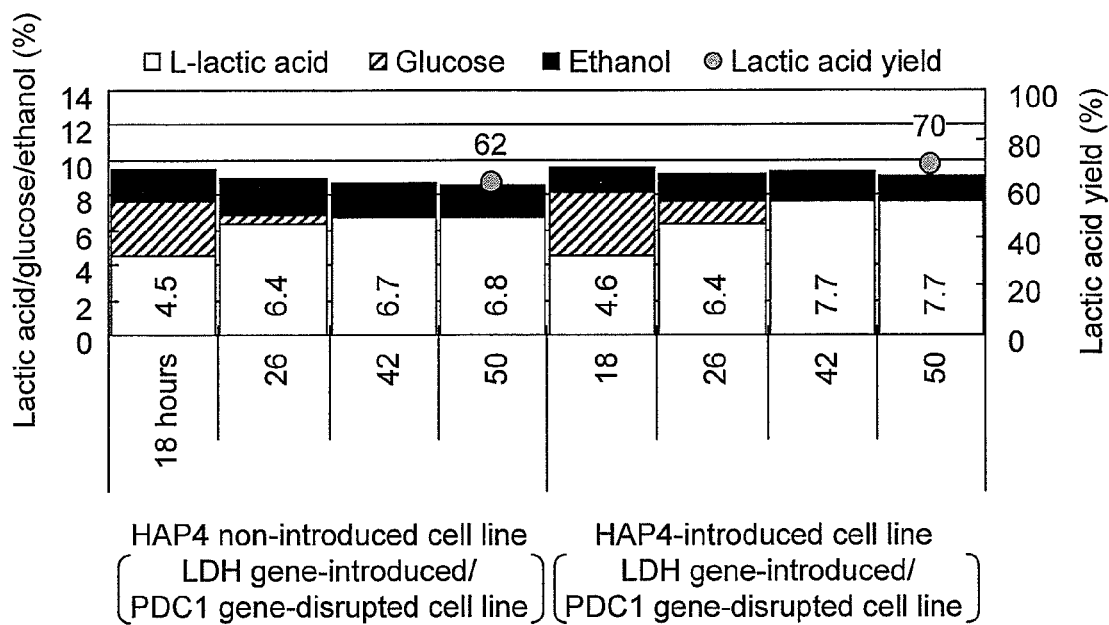
FIG. 4 is a characteristic chart showing results of a fermentation test for an HAP4-introduced cell line and an HAP4 non-introduced cell line, which are LDH gene-introduced/PDC1 gene-disrupted cell lines.

FIG. 4 shows the results of the fermentation test. As is understood from FIG. 4, in the case of the HAP4-introduced cell line, the lactic acid yield was improved from 62% to 70% and the maximum ethanol concentration decreased from 2.2% to 1.4%, compared with the HAP4 non-introduced cell line. In addition, the fermentation rate in the case of the HAP4-introduced cell line was comparable to that in the case of the HAP4 non-introduced cell line.

The above results revealed that the lactic acid production capacity is significantly improved in a yeast in which the HAP4 gene has been constitutively expressed as a result of introduction of the LDH gene serving as a foreign gene.

Fermentation Test 2

The above prepared LDH gene-introduced/PDC1 gene-disrupted and PDC5 gene-disrupted cell line (HAP4 non-introduced cell line in this test) and the LDH gene introduced/PDC1 gene-disrupted and PDC5 gene-disrupted cell line that had been introduced with the DNA fragment for HAP4 gene overexpression (HAP4-introduced cell line in this test) were subjected to a fermentation test. This fermentation test was carried out as in the case of fermentation test 1 described above, except that a YPE medium (yeast extract (1%), peptone (2%), and ethanol (1%)) was used instead of the YPD medium.

Figure 5:
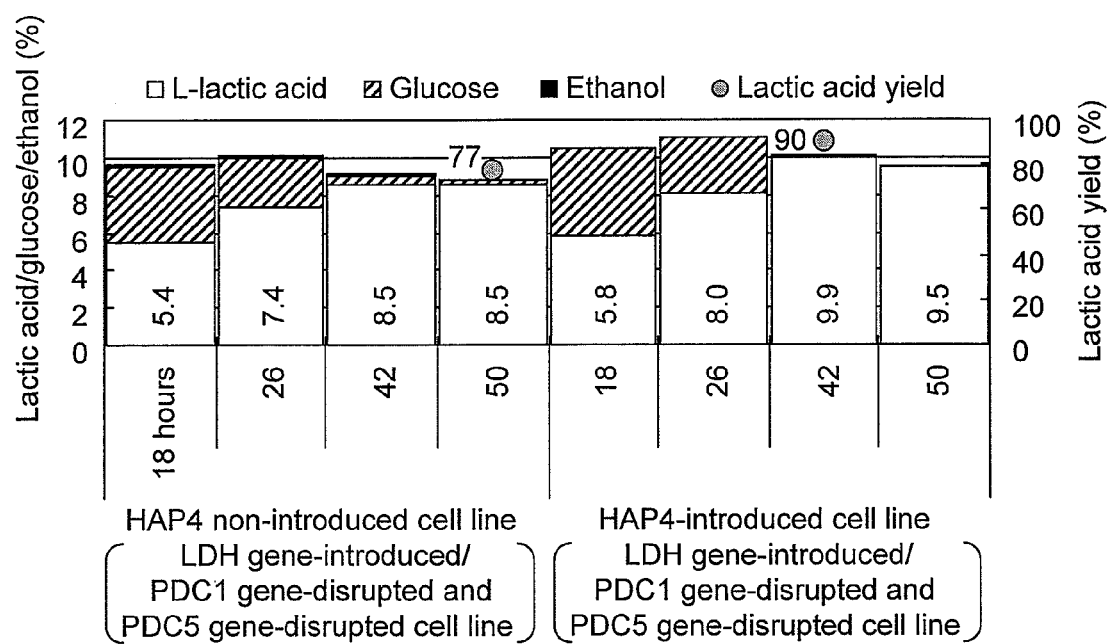
FIG. 5 is a characteristic chart showing results of a fermentation test for an HAP4-introduced cell line and an HAP4 non-introduced cell line, which are LDH gene-introduced/PDC1 gene-disrupted and PDC5 gene-disrupted cell lines.

FIG. 5 shows the results of the fermentation test. As is understood from FIG. 5, in the case of the HAP4 introduced cell line, the lactic acid yield was improved from 77% to 90% and the maximum ethanol concentration decreased from 0.09% to 0.03%, compared with the HAP4 non-introduced cell line. In addition, the fermentation rate in the case of the HAP4 introduced cell line was comparable to that in the case of the HAP4 non-introduced cell line.

The above results revealed that the lactic acid production capacity is significantly improved in a yeast, in which the HAP4 gene has been constitutively expressed, as a result of introduction of the LDH gene serving as a foreign gene. Also, the comparison of the results with the results of fermentation test 1 (FIG. 4) revealed that the lactic acid production capacity is further improved in a yeast having further lowered alcohol productivity, in which the HAP4 gene has been constitutively expressed, as a result of introduction of the LDH gene serving as a foreign gene.

All publications, patents, and patent applications cited herein are incorporated herein by reference in their entirety.

The invention claimed is:

1. A yeast mutant having lower alcohol productivity through deletion of at least one pyruvate decarboxylase gene and/or an alcohol dehydrogenase gene, wherein said at least one pyruvate decarboxylase gene is selected from the group consisting of PDC1, PDC5 and PDC6, and said alcohol dehydrogenase gene is ADH1, and wherein a foreign gene encoding a lactate dehydrogenase, and a HAP4 gene that can be constitutively expressed, have been introduced into said yeast mutant.

2. The yeast mutant of claim 1, which belongs to the genus *Saccharomyces*.

3. The yeast mutant of claim 1, which is a *Saccharomyces cerevisiae* strain.

4. A method for producing lactic acid, comprising:
culturing the yeast mutant of claim 1, to produce lactic acid; and
collecting the lactic acid.

5. A method for producing lactic acid, comprising:
culturing the yeast mutant of claim 2, to produce lactic acid; and
collecting the lactic acid.

6. A method for producing lactic acid, comprising:
culturing the yeast mutant of claim 3, to produce lactic acid; and
collecting the lactic acid.

* * * * *